US00PP31727P2

(12) United States Plant Patent
Jones

(10) Patent No.: US PP31,727 P2
(45) Date of Patent: May 5, 2020

(54) ***IPOMOEA* PLANT NAMED 'ISGHG04-1'**

(50) Latin Name: *Ipomoea batatas*
Varietal Denomination: ISGHG04-1

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/501,763

(22) Filed: Jun. 4, 2019

(51) Int. Cl.
*A01H 5/06* (2018.01)
*A01H 5/12* (2018.01)
*A01H 6/00* (2018.01)

(52) U.S. Cl.
USPC ..... Plt./258
CPC ..... *A01H 6/00* (2018.05)

(58) Field of Classification Search
USPC ..... Plt./258, 263.1, 226
CPC ..... A01H 5/02; A01H 5/06; A01H 5/12
See application file for complete search history.

*Primary Examiner* — Kent L Bell
(74) *Attorney, Agent, or Firm* — Cassandra Bright

(57) ABSTRACT

A new and distinct *Ipomoea batatas* cultivar named 'ISGHG04-1' is disclosed, characterized by bright green heart-shaped foliage, which exhibits improved resistance to sun-scald. Plants have a dense, bush forming habit and produce many lateral branches, without pinching or chemical growth regulators. The new cultivar is an *Ipomoea batatas*, typically suited for ornamental container and garden use.

2 Drawing Sheets

Latin name of the genus and species: *Ipomoea batatas*.
Variety denomination: 'ISGHG04-1'.

BACKGROUND OF THE INVENTION

The new variety originated as a chance discovery by the inventor, Steve Jones. The variety was discovered as a naturally occurring whole plant mutation from an unnamed, unpatented proprietary variety of *Ipomoea batatas*. The new variety was discovered in August 2018 at a commercial greenhouse in Santa Paula, Calif.

After selecting and isolating the new cultivar, asexual reproduction of the new cultivar 'ISGHG04-1' was first performed by vegetative tip cuttings in a commercial greenhouse in Santa Paula, Calif. in October 2018. 'ISGHG04-1' has since produced several generations and has shown that the unique features of this cultivar are stable and reproduced true to type. Typical asexual reproduction of the new variety is by vegetative tip cuttings.

SUMMARY OF THE INVENTION

The cultivar 'ISGHG04-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGHG04-1'. These characteristics in combination distinguish 'ISGHG04-1' as a new and distinct *Ipomoea* cultivar:

1. Vigorous, spreading growth habit.
2. Bright green foliage color.
3. Dense and bushy plant habit.
4. Very well branched, without pinching or chemical growth regulator use.

PARENTAL COMPARISON

Plants of the new cultivar 'ISGHG04-1' are similar to the parent in most horticultural characteristics. However, 'ISGHG04-1' differs in the following:

1. The new variety has greater plant vigor than the parent variety.

COMMERCIAL COMPARISON

Plants of the new cultivar 'ISGHG04-1' can be compared to the unpatented commercial variety *Ipomoea batatas* 'Sweet Caroline Sweetheart Lime'. Plants of 'ISGHG04-1' are similar to plants of 'Sweet Caroline Sweetheart Lime' in some horticultural characteristics, however, plants of 'ISGHG04-1' differ in the following:

1. The new variety has greater plant vigor than this comparator.
2. The new variety has less sun scalding in high light conditions than the comparator.

BRIEF DESCRIPTION OF THE PHOTOGRAPHS

Figure 1:
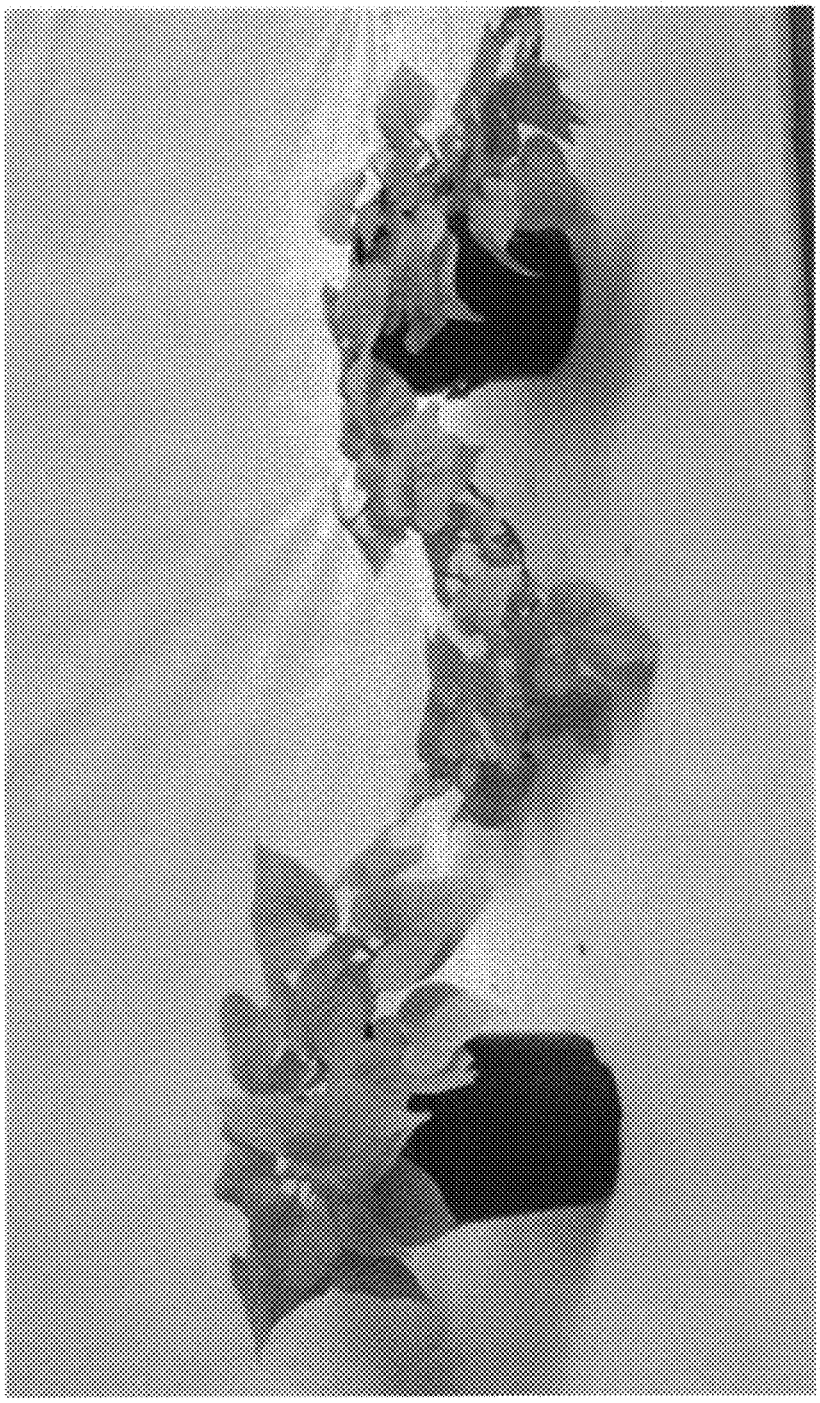

The accompanying photograph in FIG. 1 illustrates in full color a typical plant of 'ISGHG04-1', seen in the right side of the photograph. The plant on the left of the photograph is the abovementioned comparator variety 'Sweet Caroline Sweetheart Lime'. Both plants are approximately 8 weeks old, from an unrooted cutting, shown in a 6 inch pot.

Figure 2:
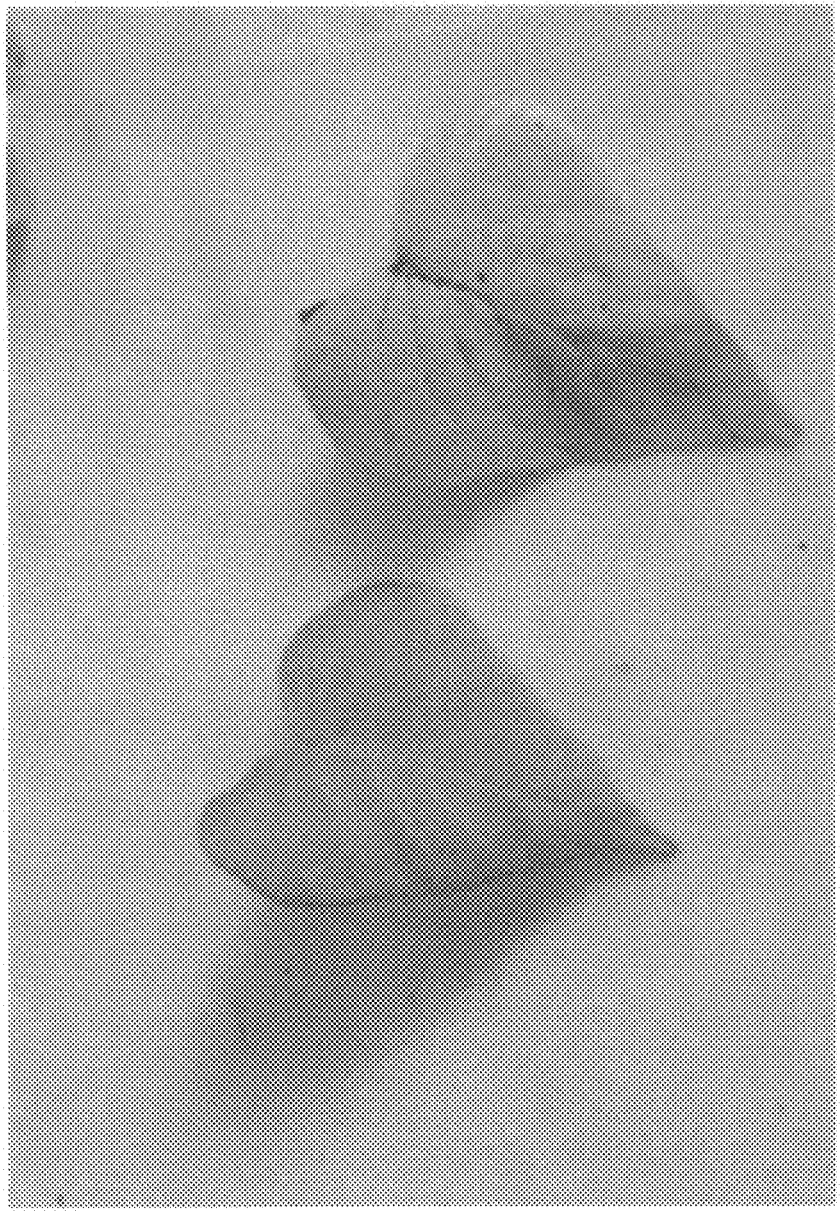

FIG. 2 illustrates a close up of the foliage of both the new variety and the abovementioned comparator. Foliage of the new variety is on the right in FIG. 2, foliage of this comparator is seen on the left side of the photograph. Plants were grown in a greenhouse in Santa Paula, Calif.

The photographs were taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2007, except where general terms of ordinary dictionary significance are used. The following observations and measurements describe 'ISGHG04-1' plants grown during the Spring months in a greenhouse in Santa Paula, Calif., under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGHG04-1'.

Age of the plant described: Approximately 8 weeks from an unrooted cutting.

Container size of the plant described: 1 gallon commercial container.

Propagation:

*Propagation method*.—Terminal cuttings.

*Time to develop roots suitable for transplanting*.—Summer — about 6 days at an average temperature of 24° C.; Winter — about 10 days at an average temperature of 24° C.

*Root description*.—Thick, fleshy. Roots colored closest to RHS Yellow-White 158A.

*Tuber description*.—Not observed to date.

Plant:

*Growth habit*.—Spreading. Dense and bushy.

*Height*.—Measured from top of soil line of pot, approximately 15 cm.

*Plant spread*.—Approximately 50 cm.

*Growth rate*.—Rapid.

*Branching characteristics*.—Very free branching, alternate or whorled occurring.

Primary lateral branches:

*Length*.—7 to 32 cm.

*Diameter*.—Approximately 0.5 cm.

*Texture*.—Glabrous to rough.

*Color*.—Near RHS Yellow-Green 145A.

*Strength*.—Strong.

*Internode length*.—0.5-2.0 cm.

*Adventitious roots at nodes*.—Not observed.

Secondary lateral branches:

*Length*.—3 to 5 cm.

*Diameter*.—Approximately 0.4 cm.

*Texture*.—Very slight rough pubescence.

*Color*.—Near RHS Yellow-Green 145A.

*Strength*.—Flexible.

*Internode length*.—0.7 to 1.0 cm.

*Quantity per* 20 *week old plant*.—Approximately 10 to 20.

*Adventitious roots at nodes*.—Not observed.

New shoot growth characteristics:

*Color*.—Near RHS Yellow-Green 145A.

*Aspect*.—Upright in center of plant, outward along outer circumference.

*Texture*.—Glabrous or somewhat rough.

Foliage:

Leaf:

*Arrangement*.—Whorled and alternate, simple.

*Average length*.—10 cm.

*Average width*.—6 cm.

*Shape of blade*.—Cordate.

*Apex*.—Acute.

*Base*.—Cordate.

*Margin*.—Entire.

*Aspect*.—Mostly flat, slight upward fold at mid-vein.

*Texture of top surface*.—Glabrous.

*Texture of bottom surface*.—Glabrous.

*Appearance of top surface*.—Matte.

*Appearance of bottom surface*.—Matte.

*Quantity of leaves per lateral branch*.—Average 10 to 25.

Foliage color:

*Young foliage upper side*.—Near RHS Yellow-Green 144B.

*Young foliage under side*.—Near RHS Yellow-Green 147D.

*Mature foliage upper side*.—Near RHS Yellow-Green 144B.

*Mature foliage under side*.—Near RHS Green 138C.

Venation:

*Type*.—Palmate, reticulate.

*Venation color upper leaf*.—Near RHS Yellow-Green N144C.

*Venation color lower leaf*.—Near RHS Yellow-Green 145B.

Petiole:

*Length*.—Average range from approximately 6 to 8 cm.

*Diameter*.—Approximately 0.3 cm.

*Texture*.—Glabrous to very slightly pubescent.

*Color*.—Near RHS Yellow-Green 145A.

*Strength*.—Moderately strong, very flexible.

*Aspect*.—Straight to slightly undulate.

Flower: Flowering not observed to date.

Other characteristics:

Seeds and fruits: No seeds/fruits observed.

Disease/pest resistance: Neither resistance nor susceptibility to the normal pests and diseases of *Ipomoea* has been observed.

Temperature tolerance: Tolerates low temperatures to approximately 2° C. Good high temperature tolerance, observed to at least 38° C.

What is claimed is:

1. A new and distinct cultivar of *Ipomoea batatas* plant named 'ISGHG04-1' as herein illustrated and described.

* * * * *